United States Patent [19]

Collington et al.

[11] Patent Number: 4,530,925
[45] Date of Patent: Jul. 23, 1985

[54] AMINOCYCLOPENTANE ESTERS AND PHARMACEUTICAL FORMULATIONS

[75] Inventors: Eric W. Collington, Welwyn; Peter Hallett; Christopher J. Wallis, both of Royston; John Bradshaw, Ware, all of England

[73] Assignee: Glaxo Group Limited, London, England

[21] Appl. No.: 589,303

[22] Filed: Mar. 14, 1984

[30] Foreign Application Priority Data

Mar. 15, 1983 [GB] United Kingdom ................. 8307099

[51] Int. Cl.[3] .................. A61K 31/535; A61K 31/54; C07D 295/14
[52] U.S. Cl. .................................... 514/211; 544/357; 544/360; 514/212; 544/364; 544/372; 514/222; 544/374; 544/379; 514/230; 544/399; 544/400; 514/232; 546/187; 546/191; 514/234; 546/205; 546/207; 514/236; 546/208; 546/213; 514/252; 546/233; 546/234; 514/255; 546/238; 546/239; 514/316; 514/317; 514/319; 514/326; 514/331; 514/422; 514/428; 544/58.1; 544/58.2; 544/58.5; 544/58.6; 544/58.7; 544/85; 544/87; 544/121; 544/130; 544/141; 544/146; 544/148; 544/158; 544/159; 544/165; 544/168; 544/171
[58] Field of Search .................... 544/58.1, 58.2, 58.5, 544/58.6, 58.7, 85, 87, 121, 130, 141, 146, 148, 158, 159, 165, 168, 171, 357, 360, 364, 372, 374, 379, 399, 400; 546/187, 191, 205, 207, 208, 213, 233, 234, 238, 239; 548/523, 527, 517, 568, 573; 260/239 BF, 243.3, 244.4, 245.7, 330.6, 330.9; 424/244, 246, 248.5, 248.51, 248.54, 248.55, 250, 267, 274, 45

[56] References Cited

U.S. PATENT DOCUMENTS

| | | | |
|---|---|---|---|
| 4,265,891 | 5/1981 | Collington et al. | 424/244 |
| 4,327,092 | 4/1982 | Collington et al. | 424/246 |
| 4,342,756 | 8/1982 | Collington et al. | 424/244 |
| 4,371,530 | 2/1983 | Collington et al. | 424/244 |
| 4,409,213 | 10/1983 | Collington et al. | 424/244 |
| 4,410,521 | 10/1983 | Collington et al. | 424/244 |
| 4,438,111 | 3/1984 | Collington et al. | 424/246 |
| 4,438,112 | 3/1984 | Collington et al. | 424/244 |
| 4,447,428 | 5/1984 | Collington et al. | 424/244 |
| 4,482,549 | 11/1984 | Collington et al. | 424/244 |

Primary Examiner—Robert W. Ramsuer
Attorney, Agent, or Firm—Bernard, Rothwell & Brown

[57] ABSTRACT

Compounds are described of the formulae (1a) and (1b)

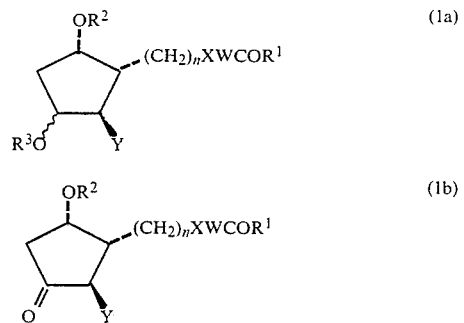

in which:
—$COR^1$ is an ester group,
n is 1 or 2,
W is $C_{1-7}$ alkylene,
X is cis or trans —CH=CH or —$CH_2CH_2$—,
Y is a saturated heterocyclic amino group,
$R^2$ is substituted or unsubstituted phenylalkyl, thienylalkyl or naphthylalkyl or cinnamyl, and
$R^3$ is —H or $C_{1-5}$ alkanoyl, including their salts.

These compounds inhibit blood platelet aggregation and bronchoconstriction and may be formulated for use as antithrombotic or antiasthmatic agents.

10 Claims, No Drawings

AMINOCYCLOPENTANE ESTERS AND PHARMACEUTICAL FORMULATIONS

The endoperoxides prostaglandins $G_2$ and $H_2$ and thromboxane $A_2$ are naturally occurring reactive metabolites of arachidonic acid in human platelets. They are not only potent aggregatory agents but are also constrictors of vascular and bronchial smooth muscle, and therefore substances which antagonise their effects are of considerable interest in human medicine.

We have now found a new group of compounds which have shown endoperoxide and thromboxane antagonist activity, and are therefore of interest in the treatment of asthma and cardiovascular diseases.

The invention thus provides compounds of the general formulae (1a) and (1b)

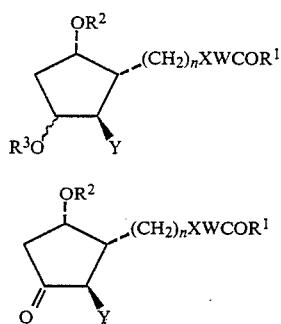

wherein $R^1$ is (a) $-OCH_2CONR^4R^5$ where $R^4$ is a hydrogen atom or $C_{1-4}$ alkyl and $R^5$ is $C_{1-4}$ alkyl or phenyl; or where $NR^4R^5$ forms a saturated heterocyclic amino group which has 5–7 ring members and optionally contains in the ring —O—(e.g. pyrrolidino, piperidino, morpholino or homomorpholino);

(b) $-OCH(CO_2R^4)_2$;

(c) $-A(CH_2)_mB(CH_2)_nR^6$ where A and B are —O— or —S—; m is 1–3, n is 0–3 and $R^6$ is phenyl;

(d) $-ACH(R^7)CO_2R^8$ where $R^7$ is a hydrogen atom, methyl or phenyl and $R^8$ is $C_{5-7}$ alkyl, $C_{5-7}$ cycloalkyl or phenyl;

(e) $-OR^9$ where $R^9$ is $C_{3-6}$ alkynyl (e.g. propynyl) or thienylmethyl;

(f) $-OCH(CH_2OH)_2$;

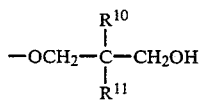

where $R^{10}$ is —OH or —CH$_2$OH and $R^{11}$ is a hydrogen atom, $C_{1-4}$ alkyl or —CH$_2$OH; or

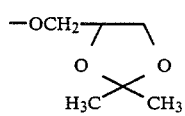

n is 1 or 2;
w is straight or branched $C_{1-7}$ alkylene;
x is cis or trans $-CH=CH-$ or $-CH_2CH_2-$;
Y is a saturated heterocyclic amino group (attached to the cyclopentane ring via the nitrogen atom) which has 5–8 ring members and (a) optionally contains in the ring —O—, —S—, —SO$_2$, or —NR$^{12}$ (where $R^{12}$ is a hydrogen atom, $C_{1-7}$ alkyl or aralkyl having a $C_{1-4}$ alkyl portion); and/or (b) is optionally substituted by one or more $C_{1-4}$ alkyl groups;

$R^2$ is (i) straight or branched $C_{1-5}$ alkyl substituted by (a) phenyl [optionally substituted by $C_{1-6}$ alkyl, $C_{5-7}$ cycloalkyl, phenylalkyl having a $C_{1-3}$ alkyl portion, thienyl or phenyl (optionally substituted by $C_{1-4}$ alkyl, $C_{1-4}$ alkoxy or phenyl)], (b) thienyl [optionally substituted by $C_{5-7}$ cycloalkyl or phenyl (optionally substituted by $C_{1-3}$ alkyl, $C_{1-3}$ alkoxy or halogen)] or (c) naphthyl (optionally substituted by $C_{1-4}$ alkyl or $C_{1-4}$ alkoxy) or (ii) cinnamyl;

$R^3$ is a hydrogen atom or $C_{1-5}$ alkanoyl; and the physiologically acceptable salts and solvates thereof.

The compounds may for example be of the formula (1a) (in which the —OR$^3$ group is in the β-position and $R^3$ is a hydrogen atom) or of the formula (1b) in which $R^1$ is a group of the types (a)–(e), and Y, X, n, W and $R^2$ are as defined above.

The structural formulae herein are to be understood to include the enantiomers of each of the compounds concerned as well as mixtures of the enantiomers including racemates, even though the precise structure as set out only relates to one enantiomer.

The amino group Y enables the compounds to form salts with organic acids e.g. maleates, or in compounds of formula (1a) with inorganic acids e.g. hydrochlorides. Also in $R^1$ groups of the type (b) where $R^4$ is a hydrogen atom salts may be formed with bases. Examples of such salts are alkali metal (e.g. sodium), alkaline earth metal (e.g. calcium) and amine (e.g. piperazine) salts.

The heterocylic amino group Y may for example have a 5, 6 or 7 membered ring, e.g. pyrrolidino, piperidino, morpholino, piperazino, thiomorpholino, 1,1-dioxothiomorpholino, homomorpholino and hexamethyleneimino. Examples of the optional substituents ($R^{12}$) which may be present on a second nitrogen atom in the ring are methyl, ethyl, butyl, hexyl, benzyl and phenethyl. The carbon atoms of the heterocyclic rings may for example be substituted by methyl, ethyl or butyl. In general, Y is preferably a saturated heterocyclic amino group having 5–8 ring members and (a) optionally contains —O— in the ring and/or (b) is optionally substituted by one or more $C_{1-4}$ alkyl groups. Preferably, Y is a morpholino or piperidino group but is particularly piperidino.

When $R^2$ is a substituted alkyl group, the alkylene portion may for example contain 1–3 carbon atoms (e.g. methylene, ethylene or propylene) and is preferably a methylene group.

In $R^2$ groups of the type (i) (a), the phenyl group may be substituted by, for example, methyl, ethyl, t-butyl, cyclohexyl, benzyl, phenethyl, or phenyl (optionally substituted by methyl, ethyl, methoxy or butoxy) groups.

In $R^2$ groups of the type (i) (b), the thienyl group may be substituted by, for example, cyclohexyl or phenyl (optionally substituted by methyl, ethyl, methoxy, ethoxy, chlorine or bromine) groups.

In general, $R^2$ is preferably a $C_{1-5}$ alkyl group substituted by phenyl which phenyl is itself substituted (preferably in the para-position) by phenyl (optionally substituted by $C_{1-4}$ alkyl or $C_{1-4}$ alkoxy).

$R^2$ is more preferably a benzyl group in which the phenyl group is substituted by thienyl or phenyl (which phenyl group itself may be optionally substituted by $C_{1-4}$ alkyl or $C_{1-4}$ alkoxy); or cinnamyl.

Particularly preferred $R^2$ groups are benzyl groups in which the phenyl portion is substituted (preferably in the para-position) by a phenyl, tolyl or methoxyphenyl group.

In the group $—(CH_2)_nXWCOR^1$, n is preferably 2.

X is preferably cis $—CH=CH—$.

W may contain for example 1–5 carbon atoms in a straight or branched chain, and is preferably $—(CH_2)_3—$ when n is 1 and $—(CH_2)_2—$ or $—(CH_2)_4—$ when n is 2.

In the $R^1$ groups, A (where present) is preferably $—O—$. $R^1$ may be for example a group of type (a) such as $—OCH_2CON(CH_3)_2—OCH_2CONHR^5$ (where $R^5$ is phenyl, methyl or ethyl) or $—OCH_2CONR^4R^5$ (where $NR^4R^5$ is morpholino); a group of type (b) such as $—OCH(CO_2CH_2CH_3)_2$; a group of type (c) such as $—OCH_2OCH_2R^6$ or $—OCH_2SCH_2R^6$; a group of type (d) such as $—OCH_2CO_2R^8$ (where $R^8$ is cyclohexyl) or a group of the type (d) in which $R^7$ is methyl and $R^8$ is $C_{5-7}$ cycloalkyl or $C_{5-7}$ alkyl; or a group of type (e) such as propynyloxy or thienylmethoxy; the group (f); or a group of the type (g) in which $R^{10}$ is $—OH$ and $R^{11}$ is a hydrogen atom or $R^{10}$ is $—CH_2OH$ and $R^{11}$ is methyl; or the group (h).

In general, $R^1$ groups of the types a,e,g, and h are preferred. Examples of preferred $R^1$ groups are $—OCH_2CON(CH_3)_2$, $—OCH_2CONR^4R^5$ where $NR^4R^5$ is morpholinyl, 2-propynyloxy, thienylmethoxy, $—OCH_2CH(OH)—CH_2OH$ and the group (h).

Particularly preferred $R^1$ groups are $—OCH_2CON(CH_3)_2$ and $—OCH_2CH(OH)CH_2OH$.

$R^3$ in the compounds of formula (1a) is preferably a hydrogen atom or acetyl, particularly a hydrogen atom.

In general, the compounds of formula (1) in which the carbon atom carrying the $—(CH_2)_nXWCOR^1$ group is in the R configuration (and mixtures containing this isomer) are preferred.

Compounds of formula (1a) in which the $—OR^3$ group is in the β-position are also generally preferred, particularly those in which the $—OR^3$ group is $—OH$.

A preferred group of compounds of the invention has the formula (1a) in which the grouop $—OR^3$ is in the β-position, and in which:

W is $—(CH_2)_2$;

n is 2;

X is cis—$CH=CH—$;

Y is piperidino or morpholino, especially piperidino;

$R^2$ is a benzyl group which the phenyl group is substituted by phenyl, which phenyl group is optionally substituted (particularly in the para position) by $C_{1-4}$ alkyl, particularly methyl, or $C_{1-4}$ alkoxy, particularly methoxy;

$R^3$ is a hydrogen atom, and $R^1$ is a group $—OCH_2CON(CH_3)_2$, 2-propynyloxy, thienylmethoxy or a group of type $—OCH_2CONR^4R^5$ (where $NR^4R^5$ is morpholinyl), or $R^3$ is a hydrogen atom or an acetyl group, especially a hydrogen atom, and $R^1$ is $OCH_2CH(OH)CH_2OH$ or a group of type (h); or $R^3$ is an acetyl group and $R^1$ is the group $OCH_2CON(CH_3)_2$ and the physiologically acceptable salts and solvates thereof.

Another preferred group of compounds has the formula (1a) in which the group $—OR^3$ is in the α-position, and in which W, n, X and $R^2$ are as just defined, Y is piperidino, $R^3$ is a hydrogen atom or an acetyl group and $R^1$ is the group $—OCH_2CON(CH_3)_2$; or $R^3$ is a hydrogen atom and $R^1$ is the group $—OCH_2CH(OH)—CH_2OH$ and the physiologically acceptable salts and solvates thereof.

Another preferred group of compounds has the formula (1b) in which W, n, X and $R^2$ are as just defined, Y is morpholino or piperidino and $R^1$ is a group $—OCH_2CH(OH)CH_2OH$ or a group of type (h), and the physiologically acceptable salts and solvates thereof.

In all three groups above, compounds in which the carbon atom carrying the $—(CH_2)_nXWCOR^1$ group is in the R configuration are particularly preferred.

The compounds of formula (1) inhibit blood platelet aggregation and bronchoconstriction. A test to determine inhibition of blood platelet aggregation is as described by G. V. Born (Nature 194, 927–929 (1962)) except in that collagen is used instead of ADP as the proaggregatory agent. Alternatively, starved guinea-pigs are dosed orally with the compound to be tested in a suitable vehicle. Platelet rich plasma is prepared from each animal and aggregation to a range of collagen concentrations is measured after the method of Born. Collagen concentration effect curves for each sample of plasma are calculated and results are expressed as the shift of the curves following treatment with the compound.

The ability of the compounds of the invention to inhibit bronchoconstriction is determined either in the anaesthetised guinea pig by measuring the effect of the compound to be tested on the dose response curve of the bronchoconstrictor [1R-[1α,4α,5β(Z), 6α(-1E,3S*)]]-7-[6-(3-hydroxy-1-octenyl)-2-oxabicyclo[2,2,1]hept-5-yl]-5-heptenoic acid (U-46619) or by the test described by K M Lulich et al in British Journal of Pharmacology 58, 71–79 (1976) except guinea pig lung or rat aorta is used instead of cat lung.

The compounds are thus of interest in the treatment of asthma, and as inhibitors of platelet aggregation and thrombosis for use in renal dialysis and the treatment and prevention of occlusive vascular diseases such as arteriosclerosis, atherosclerosis, peripheral vascular disease, cerebral vascular disease including transient ischaemic attacks, stroke, pulmonary embolism, diabetic retinopathy, post operative thrombosis, angina and myocardial infarction. They may be formulated in a conventional manner for use with one or more pharmaceutical carriers.

The compounds may be formulated for oral administration as, for example, tablets, capsules, powders, solutions or syrups prepared by conventional means with acceptable excipients.

The compounds may be formulated for parenteral administration by bolus injections or continuous infusion. Formulations for injections may be presented in unit dosage form in ampoules, or in multi-dose containers, with an added preservative.

For administration by inhalation the compounds are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount.

For use as antithrombotic agents, the compounds are preferably administered orally, for example in amounts of 0.05 to 10 mg/kg body weight, 1 to 4 times daily.

For use in the treatment of asthma, the compounds may also be administered orally in amounts of 0.05 to 10 mg/kg body weight, 1 to 4 times daily; preferably however they are administered by inhalation at doses varying from 0.3 to 30 mg, 1 to 4 times daily. The compounds may be used in combination with other antiasthmatic agents.

The precise dose administered will of course depend on the age and condition of the patient.

Suitable methods for preparing the compounds of the invention are described below, the various groups and symbols being as defined above except where otherwise indicated.

Compounds of formula (1a) and (1b) may be prepared by esterification of the corresponding carboxylic acid, i.e. a compound in which $R^1$ represents a hydroxyl group. Conventional esterification methods may be used.

Thus for example, compounds in which $R^1$ is a group of the type a, b, c or d (in which A is —O—) or e may be prepared by reacting the corresponding carboxylic acid with an appropriate halide $R^{13}$ Hal, where Hal represents halogen and $R^{13}$ as just defined for $R^1$, excluding the terminal —O—. The reaction is carried out in the presence of a suitable base, e.g. potassium t-butoxide or potassium carbonate or a sterically hindered amine such as N,N-diisopropylethylamine, triethylamine or dicyclohexylamine in a suitable solvent (such as acetonitrile, dimethylformamide, $CH_2Cl_2$ or a ketone e.g. acetone), for example at a temperature from 0° C. to room temperature.

This reaction may also be used to prepare compounds in which $R^1$ is a group of type (c) in which A is —S— and m is 1 or of type (d) in which A is —S—, by reacting the corresponding thioacid (i.e. in which $R^1$ is —SH) with an appropriate halide. The thioacid starting material may be prepared in situ by treating a reactive derivative of the corresponding carboxylic acid (e.g. a mixed anhydride, as above) with a hydrosulphide (e.g. NaHS).

Compounds in which $R^1$ is a group of the type f, g or h may be prepared by reacting the corresponding carboxylic acid with an alcohol $R^1H$ in the presence of an acid (e.g. p-toluene sulphonic acid) in a solvent (e.g. a chloroform—benzene mixed solvent) for example at any suitable temperature from room temperature up to reflux. The hydroxy groups of $R^1$ groups of types f and g should be protected in this reaction, for example in the form of a cyclic ketal.

Compounds in which $R^1$ is thienylmethoxy may also be prepared by reaction of the corresponding carboxylic acid with 2-thiophenemethanol in the presence of triphenylphosphine and diethyl azodicarboxylate in a solvent e.g. an ether-tetrahydrofuran mixture.

Many of the carboxylic acids corresponding to the esters of formula (1a) and (1b) required as starting materials for process (a) i.e. compounds of formula (1a) and (1b) in which $R^1$ is —OH are described in British Patent Specifications 2028805A, 2070591A, 2075503A and 2097397A and those containing other $R^2$ groups may be prepared by the same general methods, using starting materials containing the desired $R^2$ group.

(b) Compounds in which $R^1$ is a group of the type (g) in which $R^{10}$ is —OH and $R^{11}$ is a hydrogen atom may be prepared by treating the corresponding compound in which $R^1$ is the group (h) with an acid, e.g. a mineral acid such as hydrochloric acid.

(c) Compounds of formula (1a) in which $R^3$ is alkanoyl may be prepared by esterification of the corresponding compound in which $R^3$ is a hydrogen atom. The reaction may be performed by using a reactive derivative of the acid $R^3OH$ (e.g. an acid anhydride, acid chloride or chlorofomate) in the presence of a base (e.g. triethylamine or pyridine), for example at a temperature of 0° C. up to room temperature.

(d) The compounds of the invention in which X is —$CH_2CH_2$— may be prepared by catalytic hydrogenation of a corresponding compound in which X is —CH=CH, using a catalyst such as palladium oxide. Alcohols such as ethanol are suitable solvents and the reaction may be performed at room temperature.

(e) Compounds of formula (1b) may be prepared by oxidising a corresponding hydroxy compound e.g. a compound of formula (2)

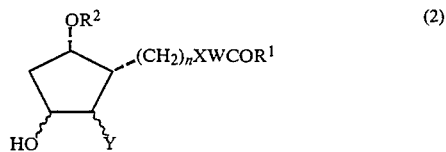

(2)

Suitable method of oxidation include using a $Cr^{VI}$ oxidising reagent in a suitable solvent, e.g. chromic acid in acetone (e.g. Jones reagent, preferably used in the presence of a diatomaceous silica such as Celite) or $CrO_3$ in pyridine. These reagents are for example used at temperatures of −20° C. to room temperature.

Other important methods include using an activated sulphur reagent, e.g. (i) N-chlorosuccinimidedimethylsulphide complex in a suitable solvent (e.g. toluene or dichloromethane) at temperatures of for example −25° to 25° C., preferably at 0°-5° C., (ii) a dialkylsulphoxide (e.g. dimethylsulphoxide) activated by a suitable electrophilic reagent (such as oxalyl chloride, acetyl bromide or thionly chloride) in a suitable solvent (e.g. toluene or dichloromethane), e.g. at 31 70° to −20° C.; dicyclohexylcarbodiimide can also be used as the electrophilic reagent (preferably in the presence of $CF_3COOH$ or its pyridinium salt) at for example −10° C. using the same solvents, or (iii) pyridine —$SO_3$ complex in dimethylsulphoxide, preferably at 0° C. to room temperature. When Y is in the α-configuration, conditions should be chosen to effect epimerisation, either at the same time or after oxidation.

The esters of formula (2) may be prepared by esterification of the corresponding carboxylic acid in which $R^1$ is a hydroxyl group, for example using the methods described above in connection with process (a).

The carboxylic acid starting materials may be prepared by the methods generally described in British Patent Specifications 2028805A, 2070591A, 2075503A and 2097397A.

Compounds of formula (1b) in which the ester group is sensitive to oxidation are preferably prepared by the esterification process (a).

(f) Compounds of formula 1(a) in which $R^3$ is a hydrogen atom and $R^1$ is a group of the type (g) where $R^{10}$ is —$CH_2OH$ and $R^{11}$ is a $C_{1-4}$ alkyl group may be prepared by hydrolysis of the corresponding ortho ester of formula (3):

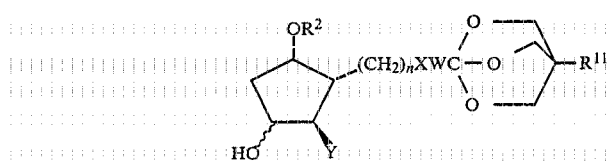

The reaction may for example be effected with ethereal hydrogen chloride in a solvent such as $CH_2Cl_2$ at e.g. room temperature. Intermediates of formula (3) may be prepared by reaction of a compound of formula (4)

with a compound (5) $Ph_3P^+CH_2WC(OCH_2)_3CR^{11}$ iodide in the presence of potassium t-butoxide in tetrahydrofuran at 0° C.

Intermediates of formula (4) may be prepared by the methods generally described in British Patent Specification 2028805A, 2075503A and 2097397A. Intermediates of formula (5) are either known compounds (E. J. Corey and Matarajam Raju, Tetrahedron Letters, 1983, vol. 24, pages 5571-74), or mayb be prepared by analogous methods to those described for the known compounds.

Compounds of formula (1b) may also be prepared by process (f) by oxidising the ring -OH prior to hydrolysis.

(g) Where salts of compounds of formula (1) are desired such salts may be formed by conventional methods, for example by treatment with an acid or when $R^1$ contains a —COOH group, with a base. Salts of acids may be prepared by adding the acid (e.g. an inorganic acid such as hydrogen chloride) to a solution of the compound of formula (1) in an organic solvent such as ether. Salts of bases may be prepared by adding the base (e.g. an amine such as piperazine) in a solvent such as ether.

When a specific enantiomer of formula (1) is required, starting materials having the desired stereochemical configuration should be used in the above processes. Such starting materials may for example be prepared from an enantiomeric bromohydrin as generally described in British Patent Specifications 2075503A and 2097397A.

The following examples illustrate the invention. Temperatures are in °C. Chromatography was carried out using silica gel unless stated otherwise. Dried refers to drying with $MgSO_4$. The following abbreviations are used:

T.l.c. Thin layer chromatography using $SiO_2$ unless stated otherwise
ER: ether
EA: ethyl acetate
DMF: diemthylformamide
PE: petroleum ether (b.p. 40°–60°)
DIBAL: diisobutylaluminium hydride
THF: tetrahydrofuran
DMSO: dimethylsulphoxide The preparations of Intermediates 1-4 are described in British Patent Specification 2075503A;

Intermediate 1

[1α(Z),2β,3α,5α]-(+)-7-[5-[[(1,1'-Biphenyl)-4-yl]methoxy]-3-hdyroxy-2-(4-morpholinyl)cyclopentyl]-4-heptenoic acid Intermediate 2

[1α(Z), 2β,5α]-(+)-7-[5-[[(1,1'-Biphenyl)-4-yl]methoxy]-2-(4-morpholinyl)-3-oxocyclopentyl]-4-heptenoic acid Intermediate 3

[1R-[1α(Z),2β,3α,5α]]-(+)-7-[5-[[(1,1'-Biphenyl)-4-yl]methoxy]-3-hydroxy-2-(4-morpholinyl)cyclopentyl]-4-heptenoic acid, hydrochloride Intermediate 4

[1R-[1α(Z),2β, 5α]]-(−)-7-[5-[[(1,1'-Biphenyl)-4-yl]methoxy]-2-(4-morpholinyl)-3-oxocyclopentyl]-4-heptenoic acid The preparations of Intermediates 5-9 are described in British Patent Specification 2097397A.

Intermediate 5

[1R-(endo,anti)]-(+)-5-hydroxy-7-(1-piperdinyl)bicyclo[2.2.1]heptan-2-one

Intermediate 6

[1R-(1α, 2β,3α,5α)]-(+)-5-[[(1,1'-Biphenyl)-4-yl]methoxy]-3-hydroxy-2-(1-piperidinyl)cyclopentane acetaldehyde Intermediate 7

[1R-[1α(Z),2β,3β,5α]]-(+)-7-[5-[[(1,1'-Biphenyl)-4-yl]methoxy]-3-hydroxy-2-(1-piperidinyl)cyclopentyl]-4-heptenoic acid Intermediate 8

[1R-[1α(Z),2β,3β,5α]]-(+)-7-[5-[[(1,1'-Biphenyl)-4-yl]methoxy]3-hydroxy-2-(4-morpholinyl)cyclopentyl]-4-heptenoic acid Intermediate 9

[1R-(1α, 2β,3β,5α)]-(+)-5-[[(1,1'-Biphenyl)-4-yl]methoxy]-3-hydroxy-2-(1-piperidinyl)cyclopentanepropanal Intermediate 10

[1R-(1α, 2β,3α,5α)]-(+)-5-[[(1,1'Biphenyl)-4-yl]methoxy]-3-hydroxy-2-(1-piperidinyl)cyclopentanepropanal A solution of Intermediate 6 (13 g) in toluene (39 ml) was added dropwise to a suspension of potassium tert-butoxide (5.9 g) in toluene (52 ml). Methoxymethyltriphenylphosphonium chloride (15.9 g) was added and the mixture stirred overnight (18 h).

2 N Hydrochloric acid (25 ml ) was added and the mixture heated with stirring at 40° for 30 min. Solid $K_2CO_3$ (13 g) was added, the organic phase separated, washed with water (52 ml) and dried azeotropiclly to give a solution of Intermediate 9 in toluene (115 ml). A portion of the solution (8.8 ml), was purified by chromatography eluting with 9:1 EA—methanol to give the title compound as a foam (0.53 g).

T.l.c 4:1 EA-methanol Rf 0.15.

$[\alpha]_D{}^{23} = 42.8°$ (CHCl$_3$).

Intermediate 11

[1R-[1α(Z),2β,3α,5α]]-(+)-7-[5-[[(1,1'-Biphenyl)-4-yl]methoxy]-3-hydroxy-2-(1-piperidinyl)cyclopentyl]-4-heptenoic acid, hydrochloride To a solution of potassium tert-butoxide (21.49 g) in toluene (198 ml) and THF (52 ml) under N$_2$ was added 3-(carboxypropyl)triphenylphosphonium bromide (41.14 g). After 1.5 h a solution of Intermediate 10 (24.5 g) in toluene (220 ml) was added and the mixture stirred for 3 h. Water (125 ml) was added, the mixture vigorously shaken and the phases separated. The aqueous phase was washed with toluene (2×225 ml) (discarded), then acidified (to pH 7.5) with 2N hydrochloric acid and extracted with CH$_2$Cl$_2$ (2×225 ml). The combined CH$_2$Cl$_2$ extracts were dried and evaporated to give the title compound, base (24.47 g) as a gum.

A solution of the base (93 mg) in CH$_2$Cl$_2$ (1.5 ml) was treated with an excess of ethereal hydrogen chloride. The solvents were removed and the residual oil triturated with ER (5 ml). The resulting solid was filtered, washed with ER and dried to give the title compound (b 92 mg) m.p. 132.5°–136° (softens at 128°). $[\alpha]_D{}^{25} = +52.9°$ (CHCl$_3$).

Intermediate 12

[1R-(endo,anti)]-(+)-5-[[4'-Methoxy(1,1'-biphenyl)-4-yl]methyl]-7-(1-piperidinyl)bicyclo[2.2.1]hepten-2-one A mixture of Intermediate 5 (30.51 g), benzyltriethylammonium chloride (6.65 g) and 4-(bromomethyl)-4'-methoxy(1,1'-biphenyl)(52.6 g) in CH$_2$Cl$_2$ (365 ml) and 17N NaOH (325 ml) was vigorously stirred at ambient temperature for 18 h. The mixture was diluted with water (1l) and extracted with CH$_2$Cl$_2$ (3×150 ml). The combined extracts were dried and evaporated and the residue was purified by chromatography using ER—PE (1:1 followed by 7:3) as eluent to give the title compound (40.2 g).

A portion was recrystallised from EA—PE m.p. 109.5°–110.5° $[\alpha]_D{}^{23.7} = +22.7$ (CHCl$_3$).

Intermediate 13

[1R-(endo,anti)]-(−)-6-[[4'-Methoxy(1,1'-biphenyl)-4-yl]methoxy]-8-(1-piperidinyl)-2-oxabicyclo[3.2.1]octan-3-one A solution of peracetic acid in acetic acid (5.6M, 124 ml) was added slowly to a stirred mixture of Intermediate 12 (42 g) in CH$_2$Cl$_2$ (235 ml), 2N H$_2$SO$_4$ (29 ml) and water (159 ml) and the mixture stirred at ambient temperature for 24 h. The mixture was adjusted to ca. pH 7 using 5N NaOH and pH 6.5 phosphate buffer then extracted with CH$_2$Cl$_2$ (3×200 ml). The combined organic extracts were added to an excess of sodium metabisulphite solution and stirred for 24 h. The mixture was extracted with EA (1×500, 2×250 ml) and the combined organic extracts were dried and evaporated and the residue was purified by chromatography using 1:1 EA-PE as eluent to give the title compound (24.4 g).

A portion was recrystallised from EA-PE m.p. 116.5°–117.5° $[\alpha]_D{}^{23.4} = -24.5$ (CHCl$_3$)

Intermediate 14

[1R-(1α,2β,3α,5α)]-3-Hydroxy-5-[[4'-methoxy(1,1'-biphenyl)-4-yl]methoxy]-2-(1-piperidinyl)cyclopentane acetaldehyde DIBAL in hexane (1M, 114 ml) was added slowly to a cold (−70°) stirred solution of Intermediate 13 (24 g) in CH$_2$Cl$_2$ (240 ml). After 0.5 h methanol (240 ml) was added, slowly at first, and the mixture was stirred at ambient temperature for 16 h. The precipitate was filtered off and the filtrate evaporated to give the title compound as a foam (24.1 g). T.l.c. 9:1 EA-methanol Rf 0.35.

Intermediate 15

[1R-(1α,2β,3α,5α)]-(+)-4-[[4'-,Methoxy(1,1'biphenyl)-4-yl]methoxy]-3-(3-methoxy-2-propenyl)-2-(1-piperidinyl)cyclopentanol, hydrochloride A solution of Intermediate 14 (24.1 g) in THF (75 ml) was added to a cooled (−5° to 0°), stirred solution of the ylid derived from methoxymethyltriphenylphosphonium chloride (78 g) and potassium tertbutoxide (25.5 g) in THF (800 ml). After 1.5 h methanol (100 ml) was added and the solvents removed in vacuo. The residue in pH 6.5 phosphate buffer (600 ml) was extracted with CH$_2$Cl$_2$ (3×150 ml) and the combined extracts were dried and evaporated. The residue was purified by chromatography using 4:1 EA-methanol as eluent to give the title compound, base as an oil (24.8 g).

A portion was converted into the hydrochloride salt m.p. 150°–151° (dec) $[\alpha]_D{}^{23.1} = +38.1$ (CHCl$_3$).

Intermediate 16

[1R-(1α,2α,3α,5α)]-(+)-3-Hydroxy-5-[[4'-methoxy(1,1'-biphenyl)-4-yl]methoxy]-2-(1-piperidinyl)cyclopentanepropanal, hydrochloride A solution of Intermediate 15 (24.3 g) in 2N HCl (55 ml) and acetone (250 ml) was stirred at ambient temperature for 1 h. Most of the acetone was removed in vacuo and the residue in water was extracted with CH$_2$Cl$_2$ (3×150 ml). The combined extracts were dried and evaporated to give a solid (23.6 g). A portion was triturated with ether to give the title compound as a powder m.p. 182°–185° (dec)
$[\alpha]_D{}^{22.7} = +51.5$ (CHCl$_3$).

Intermediate 17

[1R-[1α(Z),2β,3α,5α]]-(+)-Methyl 7-[3-Hydroxy-5-[[4'-methoxy(1,1'-biphenyl)-4-yl]methoxy]-2-(1-piperidinyl)cyclopentyl]-4-heptenoate, hydrochloride.

A suspension of Intermediate 16 (23.6 g) in THF (300 ml) was added to the ylid derived from 3-(carboxypropyl)triphenylphosphonium bromide (69.5 g) and potassium tert-butoxide (36.3 g) in THF (1000 ml). After 2 h water (200 ml) was added and the THF was removed in vacuo. The residue was diluted with water (250 ml) and extracted with ER (3×200 ml; discarded). The aqueous layer was neutralised using 5N HCl and extracted with CH$_2$Cl$_2$ (3×200 ml). The combined extracts were dried and evaporated and the residue was left to stand in methanol (250 ml) containing concentrated sulphuric acid (5 ml) for 19 h. Most of the methanol was removed in vacuo and the residue neutralised using 2N NaOH and pH 6.5 phosphate buffer (150 ml). The mixture was extracted with EA (3×150 ml) and the combined extracts were dried and evaporated. The residue was purified by chromatography using initially 9:1 ER-methanol followed by 4:1 ER-methanol as eluent to give the title compound, base as an oil (15.9 g). A portion was converted into the hydrochloride salt m.p. 122°–125° (dec).

$[\alpha]_D^{22.5} = +55.9°$ (CHCl$_3$).

Intermediate 18

[1R-[1α(Z),2β,5α]]-(−)-Methyl 7-[5-[[4'-Methoxy(1,1'-biphenyl)-4-yl]methoxy]-3-oxo-2-(1-piperidinyl)cyclopentyl]-4-heptenoate A solution of pyridine-sulphur trioxide complex (10.33 g) in dry DMSO (17 ml) was added to a cold (0°) solution of Intermediate 17, base (8.47 g) in Et$_3$N (13.5 ml), CH$_2$Cl$_2$ (30 ml) and DMSO (20 ml). After 1 h at 0° the mixture was diluted with pH 6.5 phosphate buffer (140 ml) and extracted with EA (3×50 ml). The combined extracts were dried and evaporated and the residue was purified by chromatography using 1:3 EA-PE as eluent to give the title compound as a solid (5.69 g). A portion was recrystallised from ER-PE m.p. 61.5°–62.5°.

$[\alpha]_D^{22.2} = -19.8°$ (CHCl$_3$).

Intermediate 19

[1R-[1α(Z),2β,3β,5α]]-(+)-Methyl 7-[3-Hydroxy-5-[[4'-methoxy(1,1'-biphenyl)-4-yl]methoxy]-2-(1-piperidinyl)cyclopentyl]-4-heptenoate A solution of DIBAL in hexane (1M, 93 ml) was added dropwise to a cold (−5°) stirred solution of 2,6-di-tert-butyl-4-methylphenol (30.75 g) in dry toluene (350 ml). After 1 h at −5° the mixture was cooled to −70° and a solution of Intermediate 18 (9.67 g) in toluene (50 ml) was added dropwise. After 1 h at −70° and 1 h at −10° the mixture was washed with 2N HCl (7×60 ml) and the toluene was discarded. The acidic extracts were neutralised with 5N NaOH solution (200 ml) and extracted with CH$_2$Cl$_2$ (4×80 ml). The combined extracts were dried and evaporated and the residue was purified by chromatography using 17:3 ER-methanol as eluent to give the title compound (7.02 g) as an oil.

Analysis Found: C,73.5; H,8.5; N,2.7. C$_{32}$H$_{43}$NO$_5$ requires C,73.7; H,8.3; N,2.7%.

$[\alpha]_D^{21} = +63.2°$ (CHCl$_3$).

Intermediate 20

[1R-[1α(Z),2β,3β,5α]]-(+)-7-[3-Hydroxy-5-[[4'-methoxy(1,1'-biphenyl)-4-yl]methoxy]-2-(1-piperidinyl)cyclopentyl]-4-heptenoic acid, hydrochloride A mixture of Intermediate 19 (5.89 g) 5N NaOH solution (6.77 ml) and methanol (40 ml) was vigorously stirred at ambient temperature for 18 h. Most of the methanol was removed in vacuo and the residue in pH 6.5 phosphate buffer (150 ml) was extracted with CH$_2$Cl$_2$ (3×40 ml). The combined extracts were dried and evaporated to give the title compound, base as a foam (5.79 g).

A portion (0.67 g) in ER-CH$_2$Cl$_2$ was treated with an excess of ethereal HCl to give the title compound (0.61 g) m.p. 122°–124°.

$[\alpha]_D^{21.9} = +61.2°$ (CHCl$_3$).

Intermediate 21

(3-Methyl-3-oxetanyl)methyl 4-chlorobutanoate

4-Chlorobutyryl chloride (25 ml) was added dropwise to a solution of 3-methyl-3-oxetanemethanol (20 g) and pyridine (21 ml) in CH$_2$Cl$_2$ (75 ml) at 0° under nitrogen. An exothermic reaction resulted with precipitation of pyridinium hydrochloride. After 70 min at 0° water (400 ml) was added and the mixture was extracted with CH$_2$Cl$_2$ (3×200 ml). The combined extracts were washed with pH 6 phosphate buffer (200 ml), dried and evaporated to give an oil which was purified by chromatography eluting with 1:1 EA-PE to give the title compound as an oil (40 g).

Analysis Found: C,52.0;H,7.3. C$_{19}$H$_{15}$ClO$_3$ requires C,52.3;H,7.3%.

Intermediate 22

1-(3-Chloropropyl)-4-methyl-2,6,7-trioxabicyclo[2.2.2]octane

BF$_3$.Et$_2$O (4.5 ml) was added to a stirred solution of Intermediate 21 (30 g) in CH$_2$Cl$_2$(150 ml) at −15° under nitrogen. After 16 h the mixture was allowed to warm to room temperature. Et$_3$N (10.6 ml) was added followed by ER (130 ml) and the solvents were removed in vacuo. Fresh ER (50 ml) was added and the BF$_3$-Et$_3$N complex was removed by filtration. The filtrate was evaporated in vacuo and the residue was purified by chromatography using 2:1 PE-EA containing 1% Et$_3$N as eluent to give the title compound as an oil (23.9 g).

Analysis Found: C,52.4;H,7.7. C$_9$H$_{15}$ClO$_3$ requires C,52.3;H,7.3%.

Intermediate 23

[3-(4-Methyl-2,6,7-trioxabicyclo[2.2.2]oct-1-yl)propyl]triphenyl phosphonium iodide A mixture of Intermediate 22 (5 g), triphenylphosphine (33.6 g), NaHCO$_3$ (7 g) and NaI (19.3 g) in acetonitrile (175 ml) was heated under reflux for 17 h. After cooling the inorganic solids were filtered off and washed with dichloromethane. The combined filtrates were evaporated and the residue was triturated firstly with ER (discarded) and then with CH$_2$Cl$_2$. The CH$_2$Cl$_2$ extracts were evaporated in vacuo and the residue, which solidified on trituration with ER, was crystallised from EA-acetonitrile to give the title compound (8.1 g) m.p. 189°–191°.

Intermediate 24

[1S-[1α,2α3β(Z),4β]]-(+)-4-[[(1,1'-Biphenyl)-4-yl]methoxy]-3-[6-(4-methyl-2,6,7-trioxabicyclo[2.2.2]oct-1-yl]-3-hexenyl]-2-(1-piperidinyl)cyclopentanol Intermediate 23 (5 g) was added to a stirred solution of potassium tertbutoxide (1 g) in THF (40 ml) at 0° under nitrogen followed by a solution of Intermediate 9 (0.9 g) in THF (7 ml) 10 min later. After a further 1 h water (200 ml) was added and the mixture was extracted with EA (3×130 ml). The combined extracts were washed with water (200 ml), dried and evaporated and the residue was purified by chromatography using 2:1 EA-PE containing 1% Et$_3$N as eluent to give the title compound as an oil (0.235 g).

Analysis Found: C,74.6;H,8.8;N,2.5. C$_{35}$H$_{47}$NO$_5$ requires C,74.8;H,8.4;N,2.5%.

$[\alpha]D19.8 = +61.4°$ (CHCl$_3$).

EXAMPLE 1

(a)

[1R-[1α(Z),2α,3β,5α]]-(+)-2-(Dimethylamino)-2-oxoethyl 7-[5-[[(1,1'-Biphenyl)-4-yl]methoxy]-3-hydroxy-2-(1-piperidinyl)cyclopentyl]-4-heptenoate A solution of Intermediate 7 (0.5 g), 2-Bromo-N,N-dimethyl acetamide (0.485 g) and diisopropylethylamine (0.68 ml) in acetone (10 ml) was kept at 20° for 20 h. The solvent was removed in vacuo and the residue in pH 6.5 phosphate buffer (100 ml) was extracted with EA (3×50 ml). The combined extracts were dried and evaporated and the residue was purified by chromatography using 99:1 EA-Et$_3$N as eluent to give the title compound which solidified on cooling (0.43 g), m.p. 42°–44°.

Analysis Found: C,72.7;H,8.35;N,4.9. C$_{34}$H$_{46}$N$_2$O$_5$ required C,72.6;H,8.2;N,5.0%.

$[\alpha]_D^{23.5} = +63.1°$ (CHCl$_3$).

The following compounds were prepared in a similar manner:

(b)

[1R-[1α(Z),2β,3β,5α]]-(+)-2-Oxo-2-(phenylamino)ethyl 7-[5-[[(1,1'-Biphenyl)-4-yl]methoxy]-3-hydroxy-2-(1-piperidinyl)cyclopentyl]-4-heptenoate, from Intermediate 7 and 2-bromo-N-phenyl acetamide Purification by chromatography using 99:1 ER-Et$_3$N. T.l.c. 99:1 ER-Et$_{3N}$, Rf 0.19.

Analysis Found: C,74.2;H,7.7;N,4.4. C$_{38}$H$_{46}$N$_2$O$_5$ requires C,74.7;H,7.6;N,4.6%.

$[\alpha]_D^{21.9} = +53.4°$ (CHCl$_3$).

(c) [1R-[1α(Z),2β,5α]]-(+)-phenylmethoxy)methyl 7-[5-[[1,1'-Biphenyl)'-4-yl]methoxy]-3-hydroxy-2-(1-piperidinyl)cyclopentyl]-4-heptenoate, from Intermediate 7 and chloromethyl benzyl ether.

Purification by chromatography on alumina using 1:1 EA-PE. T.l.c. (Al$_2$O$_3$) 1:1 EA-PE, Rf 0.35

Analysis Found: C,76.0;H,8.1;N,2.8. C$_{38}$H$_{47}$NO$_5$ requires C,76.4;H,7.9;N,2.3%.

$[\alpha]_D^{23} = +53.8°$ (CHCl$_3$).

(d) [1R-[1α(Z),2β,3β,5α]]-(+)-Diethyl) 2-[[7-[5-[[(1,1-Biphenyl)-4-yl]methoxy]-3-hydroxy-2-(1-piperidinyl)cyclopentyl]-1-oxo-4-heptenyl]oxy]-1,3-propanedioate, from Intermediate 7 and diethylbromo malonate.

Purification by chromatography using 90:10:1 CH$_2$Cl$_2$—ER—Et$_3$N followed by 150:50:1 CH$_2$Cl$_2$—ER—Et$_3$N. T.l.c. 49:1 EA-Et$_3$N, Rf 0.41.

I.r. (Neat) 3400–3100 (v.br.), 1765 (sh.), 1745 cm$^{-1}$.

$[\alpha]_D^{22.5} = +56.6°$ (CHCl$_3$).

(e)

[1R-[1α(Z),2β,3α,5α]]-(+)-2-(Dimethylamino)-2-oxoethyl 7-[5-[[(1,1-Biphenyl)-4-yl]methoxy]-3-hydroxy-2-(1-piperidinyl)cyclopentyl]-4-heptenoate, hydrochloride, m.p. 100°–102° from Intermediate 11, base and 2-bromo-N,N-dimethyl acetamide Purification initially by chromatography using gradient elution from EA through to 4:1 EA-methanol. A portion of the base (100 mg) in ER-CH$_2$Cl$_2$ was treated with an excess of ethereal hydrogen chloride and the solvents removed in vacuo. The residual gum was triturated with ER to give the title compound as a solid (104 mg).

Analysis Found: C,68.0;H,7.7;N,4.5. C$_{34}$H$_{46}$N$_2$O$_5$.HCl requires C,68.15;H,7.9;N,4.7%.

$[\alpha]_D^{23} = +51.1°$ (CHCl$_3$).

(f)

[1R-[1α(Z),2β,3β,5α]]-(+)-2-Cyclohexyloxy-2-oxoethyl, 7-[5-[[(1,1'-Biphenyl)-4-yl]methoxy]-3-hydroxy-2-(1-piperidinyl)cyclopentyl]-4-heptenoate, m.p. 37°–38° from Intermediate 7 and cyclohexyl 2-bromo acetate Purification by chromatography using 95:4:1 EA-methanol-Et$_3$N.

Analysis Found: C,73.9;H,8.5;N,2.2. C$_{38}$H$_{51}$NO$_6$ requires C,73.9;H,8.3;N,2.3%.

$[\alpha]_D^{25.1} = +54.9°$ (CHCl$_3$). (g) [1R-[1α(Z),2β,3β,5α]]-(+)-2-(4-Morpholinyl)-2-oxethyl 7-[5-[[(1,1'-Biphenyl)-4-yl]methoxy]-3-hydroxy-2-(1-piperidinyl)-cyclopentyl]-4-heptenoate, from Intermediate 7 and 4-(2-bromo-1-oxoethyl)morpholine Purification by chromatography using 90:9:1 EA-methanol-Et$_3$N. T.l.c. 90:9:1 EA-methanol-Et$_3$N Rf 0.3.

I.r. (CHBr$_3$) 3600–3100, 1740, 1633 cm$^{-1}$ $[\alpha]_D^{21.8} = +58°$ (CHCl$_3$).

(h)

[1R-[1α(Z),2β,3β,5α]]-(+)-2-(Dimethylamino)-2-oxoethyl 7-[5-[[(1,1'-Biphenyl)'-4-yl]methoxy]-3-hydroxy-2-(4-morpholinyl)cyclopentyl]-4-heptenoate, m.p. 74°–76° from Intermediate 8 and 2-bromo-N,N-dimethyl acetamide Purification by chromatography using 9:1 EA-methanol. T.l.c. 9:1 EA-methanol Rf 0.34.

$[\alpha]_D^{22.2} = +53.9°$ (CHCl$_3$).

(i) [1α(Z),2β,5α]-(±)-2-propynyl 7-[5-[[(1,1'-Biphenyl)-4-yl]methoxy]-2-(4-morpholinyl)-3-oxocyclopentyl]-4-heptenoate, from Intermediate 2 and propargyl bromide Purification by chromatography using 7:3 ER-PE (b.p. 60°–80°).

I.r. (CHBr$_3$) 3290, 2120, 1735 cm$^{-1}$

Analysis Found: C,74.5;H,7.3;N,2.8. C$_{32}$H$_{37}$NO$_5$ required C,74.6;H,7.2;N,2.7%.

(j) [1α(Z),2β,5α]-(±)-2-(Dimethylamino)-2-oxoethyl 7-[5-[[(1,1'-Biphenyl-4-yl]methoxy[-2-(4-morpholinyl)-3-oxocyclopenyl]-4-heptenoate, from Intermediate 2, and 2-bromo-N,N-dimethyl acetamide Purification by chromatography (twice) using firstly 9:1 EA-methanol and secondly 7:1 ER-acetone. T.l.c. EA Rf 0.13.

I.r. (Neat) 3460 (br), 1740, 1670 cm$^{-1}$.

(k)

[1R-[1α(Z),2β,5α]-(−)-2-(Dimethylamino)-2-oxoethyl 7-[5-[[(1,1'-Biphenyl)-4-yl]methoxyl]-2-(4-morpholinyl)-3-oxocyclopentyl]-4-heptenoate, from Intermediate 4, piperdine salt, and 2-bromo-N,N-dimethyl acetamide Purification by chromatography (twice) using firstly 9:1 EA-methanol and secondly 7:1 ER-acetone. T.l.c. EA Rf 0.13.

I.R. (Neat) 3460 (br), 1740, 1670 cm$^1$.

$[\alpha]_D^{25.6} = -3.7°$ (CHCl$_3$).

EXAMPLE 2

[1R-[1α(Z),2β,3β,5α]]-(+)-(2-Thienylmethyl) 7-[5-[[(1,1'-Biphenyl)-4-yl]methoxy]-3-hydroxy-2-(1-piperidinyl)cyclopentyl]-4-heptenoate A solution of Intermediate 7 (0.51 g) in dry DMF (5 ml) was treated with 2-(bromomethyl)thiophene (0.85 g) and diisopropylethylamine (0.95 ml) in portions over 2h. After a further 1h the mixture was diluted with pH 6.5 phosphate buffer (135 ml) and extracted with $CH_2Cl_2$ (3×25 ml). The combined extracts were dried and evaporated and the residue was purified by chromatography on alumina using 1:1 EA-PE as eluent to give the title compound as an oil (0.16 g). T.l.c. ($Al_2O_3$) 1:1 EA-PE, Rf 0.6.

I.r. (Neat) 3400 (br), 1740 $cm^{-1}$
$[\alpha]_D^{23.5} = +54.2°$ ($CHCl_3$).

EXAMPLE 3

[1R-[1α(Z),2β,3β,5α]]-(+)-2-propynyl 7-[5-[[(1,1'-Biphenyl)-4-yl]methoxy-3-hydroxy-2-(1-piperidinyl)cyclopentyl]-4-heptenoate A solution of Intermediate 7 (0.3 g), diisopropylethylamine (0.44 ml) and propargyl bromide (0.21 ml; 80% solution in toluene) in acetone (5 ml) was kept at 20° for 24h. The mixture was diluted with pH 6.5 phosphate buffer (60 ml) and extracted with $CH_2Cl_2$ (3×25 ml). The combined extracts were dried and evaporated and the residue was purified on alumina using 1:1 EA-PE as eluent to give the title compound as an oil (0.13 g). T.l.c. ($Al_2O_3$) 1:1 EA-PE, Rf 0.46.

I.r. (Neat) 3400 (br), 3390, 1740 $cm^{-1}$
$[\alpha]_D^{23} = +63.6°$ ($CHCl_3$).

EXAMPLE 4

[1R-[1α(Z),2β,3β,5α]]-(+)-2-(Dimethylamino)-2-oxoethyl 7-[3-Hydroxy-5-[[4'-methoxy(1,1'-biphenyl)-4-yl]methoxy]-2-(1-piperidinyl)cyclopentyl]-4-heptenoate A solution of Intermediate 20 base, (0.6 g), 2-bromo-N,N-dimethyl acetamide (0.587 g) and diisopropylethylamine (0.82 ml) in acetone (15 ml) was kept at ambient temperature for 22 h. The solution was diluted with pH 6 phosphate buffer (50 ml) and extracted with EA (3×50 ml). The combined extracts were dried and evaporated and the residue was purified by chromatography using 99:1 EA-$Et_3N$ as eluent to give the title compound as a gum (0.595 g). T.l.c. 99:1 EA-$Et_3N$ Rf 0.1

I.r. (Neat) 3450, 1745, 1675 $cm^{-1}$
$[\alpha]_D^{20} = +62°$ ($CHCl_3$).

EXAMPLE 5

(a)

[1R-[1α(Z),2β,3β,5α]]-(+)-2-(Dimethylamino)-2-oxoethyl 7-[3-(Acetyloxy)-5-[[(1,1'-Biphenyl)-4-yl]methoxy]-2-(1-piperidinyl) cyclopentyl]-4-heptenoate $Ac_2O$ (0.6 ml) was added to a cold (0°) stirred solution of the compound of Example 1a (0.4 g) in pyridine (6 ml). After 3.5 h the solution was evaporated in vacuo and the residue in 8% $NaHCO_3$ solution (100 ml) was extracted with EA (3×50 ml). The combined extracts were washed with brine (100 ml) dried and evaporated and the residue was purified by chromatography using 99:1 EA-$Et_3N$ as eluent to give the title compound as an oil (0.4 g).

I.r. ($CHBr_3$) 1725, 1665 $cm^{-1}$
Analysis Found: C,71.0;H,8.2;N,4.7. $C_{36}H_{48}N_2O_6$ requires C,71.5;H,8.0;N,4.6%.
$[\alpha]_D^{21} = +83.5°$ ($CHCl_3$).

The following compounds were prepared in a similar manner (b)

[1R-[1α(Z),2β,3α,5α]]-(+)-2-(Dimethylamino)-2-oxoethyl 7-[3-(Acetyloxy)-5-[[(1,1'-biphenyl)-4-yl]methoxy]-2-(1-piperidinyl) cyclopentyl]-4-heptenoate, from the compound of Example 1e.

Purification by chromatography using ER then 19:1 ER-methanol.

I.r. ($CHBr_3$) 1722, 1662 $cm^{-1}$
Analysis Found: C,71.2;H,8.3;N,4.4 $C_{36}H_{48}N_2O_6$ requires C,71.5;H,8.0;N,4.6%.
$[\alpha]_D^{22.9} = +25°$ ($CHCl_3$).

(c)

[1R-[1α(Z),2β,3β,5α]]-(+)-2-(Dimethylamino)-2-oxoethyl 7-[3-(Acetyloxy)-5-[[4'-methoxy)1,1'-biphenyl)-4-yl]methoxy]-2-(1-piperidinyl)cyclopentyl]-4-heptenoate, from the compound of Example 4

Purification by chromatography using 99:1 EA-$Et_3N$.

I.r. ($CHBr_3$) 1728, 1618 $cm^{-1}$
Analysis Found: C,69.5;H,8.0;N,4.3. $C_{37}H_{50}N_2O_7$ requires C,70.0;H,7.9;N,4.4%.
$[\alpha]_D^{19} = +85.7°$ ($CHCl_3$).

(d) [1R-[1α(Z),2β,3β,5α]]-(+)-(2-Thienylmethyl) 7-[3-(Acetyloxy]-5-[[(1,1'-biphenyl)-4-yl]methoxy]-2-(1-piperidinyl)cyclopentyl]-4-heptenoate, from the compound of Example 2

Purification by chromatography using ER.
I.r. (Neat) 1735 $cm^{-1}$
Analysis Found: C,72.0;H,7.4;N,2.3. $C_{37}H_{45}NO_5S$ requires C,72.2;H,7.8;N,2.5%
$[\alpha]_D^{22.5} = +80.3°$ ($CHCl_3$).

EXAMPLE 6

[1α(Z),2β,5α]-(±)-(2-Thienylmethyl) 7-[5-[[(1,1'-Biphenyl-4-yl]methoxy]-2-(4-morpholinyl)-3-oxocyclopentyl]-4-heptenoate A solution of triphenylphosphine (0.26 g) and 2-thiophenemethanol (0.18 g) in ER (4 ml) was added to a solution of Intermediate 2 (0.48 g) and diethyl azodicarboxylate (0.18 g) in 1:1 ER-THF (8 ml). Further quantities of triphenylphosphine (0.26 g), 2 thiophenemethanol (0.18 g) and diethyl azodicarboxylate (0.18 g) in either (4 ml) were added after 20 and 25 h. After 30 h the mixture was evaporated to dryness and the residue was purified by chromatography (twice) firstly using 7:3ER-PE and secondly 1:1 EA-PE as eluents to give the title compound as an oil (0.378 g).

I.r. ($CHBr_3$) 1735 $cm^{-1}$
Analysis Found: C,70.8;H,6.9;N,2.6. $C_{34}H_{39}NO_4S$ requires C,71.2;H,6.9;N,2.4%.

EXAMPLE 7

[1R-[1α(Z),2β,3β,5α]]-(+)-(2,3-Dihydroxypropyl) 7-[5-[[(1,1'-Biphenyl)-4-yl]methoxy]-3-hydroxy-2-(1-piperidinyl)cyclopentyl]-4-heptenoate A solution of Intermediate 7 (0.5 g) in 2,2-dimethyl-1,3-dioxolane-4-methanol (10 ml) and ethereal hydrogen chloride (10 ml) was kept at ambient temperature overnight then the solvents were removed in vacuo. The residue was left with 2N HCl (15 ml) at ambient temperature for 18 h. The solution was diluted with 8% NaHCO$_3$ solution (100 ml) and extracted with CH$_2$Cl$_2$ (5×30 ml). The combined extracts were dried and evaporated and the residue was purified by chromatography using 92:5:3 ER-methanol-ET$_3$N as eluent to give the title compound as an oil (0.229 g).

I.r. (CHBr$_3$) 3590, 1728 cm$^{-1}$

Analysis Found: C,71.5;H,8.5;N,2.6. C$_{33}$H$_{45}$NO$_6$ requires C,71.8;H,8.2;N,2.5%.

$[\alpha]_D^{20.2} = +60.8°$ (CHCl$_3$).

EXAMPLE 8

(a)

[1R-[1α(Z),2β,3β,5α]]-(+)-(2,2-Dimethyl-1,3-dioxolan-4-yl)methyl
7-[5-[[(1,1'-Biphenyl)-4-yl]methoxy]-3-hydroxy-2-(1-piperidinyl) cyclopentyl]-4-heptenoate A mixture of Intermediate 7 (0.8 g), 2,2-dimethyl-1,3-dioxolane-4-methanol (8 ml), anhydrous p-toluene sulphonic acid (0.294 g), chloroform (10 ml) and benzene (50 ml) was heated under reflux for 3 h using a Dean and Stark apparatus. The cooled solution was washed with 8% NaHCO$_3$ solution (50 ml) and the phases separated. The aqueous layer was extracted with CH$_2$Cl$_2$ (3×30 ml). The combined organic layers were dried and evaporated and the residue was purified by chromatography initially on alumina (Activity 2) using ER as eluent then on silica using 97.3 EA-Et$_3$N as eluent to give the title compound as an oil (0.55 g).

I.r. (CHBr$_3$) 3400–2700, 1730 cm$^{-1}$

Analysis Found: C,72.8;H,8.75;N,2.7. C$_{36}$H$_{49}$NO$_6$ requires C,73.1;H,8.35;N,2.4%.

$[\alpha]_D^{23.1} = +57.3°$ (CHCl$_3$).

The following compounds were prepared in a similar manner.

(b)

[1R-[1α(Z),2β,3α,5α]]-(+)-(2,2-Dimethyl-1,3-dioxolan-4-yl)methyl
7-[5[[(1,1'-Biphenyl)-4-yl]methoxy]-3-hydroxy-2-(1-piperidinyl) cyclopentyl]-4-heptenoate, m.p. 44°–46° from Intermediate 11

Purification by chromatography using 9.1 ER-methanol.

Analysis Found: C,73.3;H,8.2;N,2.4 C$_{36}$H$_{49}$NO$_6$ requires C,73.6;H,8.2;N,2.4%. $[\alpha]_D^{20} = +55°$ (CHCl$_3$).

(c)

[1R-[1α(Z),2β,3β,5α]]-(+-(2,2-Dimethyl-1,3-dioxolan-4-yl)methyl
7-[3-Hydroxy-5-[[4'-methoxy)1,1'-biphenyl)-4-yl]methoxy]-2-(1-piperidinyl)cyclopentyl]-4-heptenoate, from Intermediate 20, base Purification by chromatography using gradient elution with EA, then 19:1 EA-ethanol, then 9:1 EA-ethanol. T.l.c. 9:1 EA-ethanol Rf 0.27.

I.r. (Neat) 3600–3100, 1735 cm$^{-1}$.

$[\alpha]_D = +55°$ (CHCl$_3$).

(d)

[1R-[1α(Z),2β,3α,5α]]-(+)-(2,2-Dimethyl-1,3-dioxolan-4-yl)methyl
7-[5-[[(1,1'-Biphenyl)-4-yl]methoxy]-3-hydroxy-2-(4-morpholinyl) cyclopentyl]-4-heptenoate, from Intermediate 3.

Purification by chromatography using 9:1 ER-methanol.

I.r. (CHBr$_3$) 3600–3350, 1730 cm$^{-1}$

Analysis Found: C,70.4;H,8.15;N,2.6. C$_{35}$H$_{47}$NO$_7$ requires C,70.8;H,8.0;N,2.4%.

$[\alpha]_D^{22.7} = +55.4°$ (CHCl$_3$).

(e)

[1α(Z),2β,3α,5α]-(±)-(2,2-Dimethyl-1,3-dioxolan-4-yl)methyl
7-[5-[[(1,1'-Biphenyl)-4-yl]methoxy]-3-hydroxy-2-(4-morpholinyl) cyclopentyl]-4-heptenoate, from Intermediate 1

Purification by chromatography using 9:1 ER-methanol. T.l.c. 9:1 ER-methanol Rf 0.52.

I.r. (CHBr$_3$) 3600–3400, 1730 cm$^{-1}$.

EXAMPLE 9

(a) [1R-[1α(Z),2β,3β,5α]]-(+)-(2,3-Dihydroxypropyl) 7-[3-Hydroxy-5-[[4'-methoxy(1,1'-biphenyl-9-4-yl]methoxy]-2-(1-piperidinyl)cyclopentyl]-4-heptenoate A solution of the compound of Example 8 c (0.295 g) in acetone (20 ml) and 0.5N HCl (6 ml) was kept at ambient temperature for 56 h. The solution was diluted with 8% NaHCO$_3$ solution (40 ml) and extracted with EA (3×40 ml). The combined extracts were dried and evaporated and the residue was purified by chromatography using 99:1 EA-Et$_3$N then 90:9:1 EA-ethanol-Et$_3$N as eluents to give the title compound as an oil (0.168 g).

I.r. (CHBr$_3$) 3580, 1730 cm$^{-1}$

Analysis Found: C,69.9;H,8.5;N,2.5. C$_{34}$H$_{47}$NO$_7$ requires C,70.2;H,8.1;N,2.4%.

$[\alpha]_D^{20} = +50°$ (CHCl$_3$).

The following compound was prepared in a similar manner.

(b) [1R-[1α(Z),2β,3α,5α]]-(+)-(2,3-Dihydroxypropyl) 7-[5-[[(1,1'-Biphenyl)-4-yl]methoxy]-3-hydroxy-2-(1-piperidinyl)cyclopentyl]-4-heptenoate, from the compound of Example 8b Purification by chromatography using 85:15:1 ER-methanol-Et$_3$N. T.l.c. 90:10:1 ER-methanol-Et$_3$N Rf 0.18.

I.r. (CHBr$_3$) 3590 (br), 1730 cm$^{-1}$ $[\alpha]_D^{21.2} = +51°$ (CHCl$_3$).

EXAMPLE 10

(a)

[1R-[1α(Z),2β,5α]]-(−)-(2,2-Dimethyl-1,3-dioxolan-4-yl)methyl
7-[5-[[(1,1'-Biphenyl)-4-yl]methoxy]-2-(4-morpholinyl)-3-oxocyclopentyl]-4-heptenoate A solution of pyridine-sulphur trioxide complex (1.5 g) in DMSO (9 ml) was added to a cold (0°) stirred solution of the compound of Example 8d (1.15 g) in CH$_2$Cl$_2$ (10 ml) containing Et$_3$N (4 ml). After 1 h at 0° and 2 h at ambient temperature the mixture was poured into water (60 ml) and extracted with ER (2×50 ml).

The combined extracts were washed with water (30 ml), 1M citric acid solution (20 ml) and water (20 ml) then dried and evaporated. The residue was purified by chromatography using ER as eluent to give the title compound as an oil (0.255 g).

I.r. (CHBr$_3$) 1730 cm$^{-1}$.

Analysis Found: C,71.2;H,7.85;N,2.5. C$_{35}$H$_{45}$NO$_7$ requires C,71.0;H,7.7;N,2.4%.

$[\alpha]_D^{23.1} = -7.4°$ (CHCl$_3$).

The following compound was prepared in a similar manner.

(b)
[1α(Z),2β,5α]-(±)-(2,2-Dimethyl-1,3-dioxolan-4-yl)methyl 7-[5-[[(1,1'-Biphenyl)-4-yl]methoxy]-2-(4-morpholinyl)-3-oxocyclopentyl]-4-heptenoate, from the compound of Example 8e Purification by chromatography using ER. T.l.c. ER Rf 0.36.

I.r. (CHBr$_3$) 1730 cm$^{-1}$.

EXAMPLE 11

(a) [1R-[1α(Z),2β,5α]]-(−)-(2,3-Dihydroxypropyl) 7-[5-[[(1,1'-Biphenyl)-4-yl]methoxy]-2-(4-morpholinyl)-3-oxocyclopentyl]-4-heptenoate A solution of the compound of Example 10a (0.99 g) in acetone (40 ml) containing 0.5M HCl (20 ml) was kept at ambient temperature for 4 h. The mixture was diluted with 8% NaHCO$_3$ solution (50 ml) and extracted with CH$_2$Cl$_2$ (3×50 ml). The combined extracts were dried and evaporated and the residue was purified by chromatography using 19:1 ER-methanol as eluent to give the title compound as an oil (0.55 g). T.l.c. 19:1 ER-methanol Rf 0.25.

I.r. (CHBr$_3$) 3580, 1735 cm$^{-1}$ $[\alpha]_D^{24.9} = -10.9°$ (CHCl$_3$).

The following compound was prepared in a similar manner.

(b) [1α(Z),2β,5α]-(±)-(2,3-Dihydroxypropyl) 7-[5-[[(1,1'-Biphenyl)-4-yl]methoxy]-2-(4-morpholinyl)-3-oxocyclopentyl]-4-heptenoate, from the compound of Example 10b. Purification by chromatography using 19:1 ER-methaol as eluent. T.l.c. 19:1 Er-methanol Rf 0.25.

I.r. (CHBr$_3$) 3580, 1735 cm$^{-1}$.

EXAMPLE 12

[1R-[1α(Z),2β,3β,5α]]-(+)-3-Hydroxy 2-(hydroxymethyl)-2-methylpropyl 7-[5-[[(1,1'-Biphenyl)-4-yl]methoxy]-3-hydroxy-2-(1-piperidinyl) cyclopentyl]-4-heptenoate A solution of Intermediate 24 (0.13 g) in CH$_2$Cl$_2$ (1.5 ml) containing ethereal hydrogen chloride (0.1 ml) was kept at room temperature for 15 min. The solvents were removed in vacuo and the residue in pH 6.5 phosphate buffer (15 ml) was extracted with CH$_2$Cl$_2$ (3×8 ml). The combined extracts were dried and evaporated and the residue was purified by chromatography using 99:1 EA-Et$_3$N as eluent to give the title compound as an oil which solidified on trituration with PE (45 mg), m.p. 75°-80°.

I.r. 3610, 3520 (br), 1725 cm$^{-1}$ $[\alpha]_D^{20.2} = +55.1°$ (CHCl$_3$).

Pharmaceutical Examples

Tablets

These may be prepared by direct compression or wet granulation. The direct compression method is preferred but may not be suitable in all cases as it is dependent upon the dose level and physical characteristics of the active ingredient.

A.
Direct Compression
Active Ingredient
Microcrystalline Cellulose B.P.C.
Magnesium Stearate
Compression Weight The active ingredient is sieved through a 250 m$^{-6}$ sieve, blended with the excipients and compressed using 10.00 mm punches. Tablets of other strengths may be prepared by altering the compression weight and using punches to suit.

B.
Wet granulation
Active Ingredient
Lactose B.P.
Starch B.P.
Pregelatinised Maize Starch B.P.
Magnesium Stearate B.P.
Compressed Weight The active ingredient is sieved through a 250 m$^{-6}$ sieve and blended with the lactose, starch and pre-gelatinised starch. The mixed powders are moistened with purified water, granules are made, dried, screened and blended with the magnesium stearate. The lubricated granules are compressed into tablets as described for the direct compression formula.

The tablets may be film coated with suitable film forming materials, e.g. methyl cellulose or hydroxylpropyl methyl cellulose using standard techniques. Alternatively the tablets may be sugar coated.

Capsules
Active ingredient
*STA-RX 1500
Magnesium Stearate B.P.
Fill Weight

*A form of directly compressible starch supplied by Colorcorn Ltd., Orpington, Kent.

The active ingredient is sieved through a 250 m$^{-6}$ sieve and blended with the other materials. The mix is filled into No. 2 hard gelatin capsules using a suitable filling machine. Other doses may be prepared by altering the fill weight and if necessary changing the capsule size to suit.

Inhalation cartridges
Active ingredient (micronised)
Lactose B.P. to

The active ingredient is micronised in a fluid energy mill to a fine particle size range prior to blending with normal tableting grade lactose in a high energy mixer. The powder blend is filled into No. 3 hard gelatin capsules on a suitable encapsulating machine. The contents of the cartridges are administered using a powder inhaler.

Metered Dose Pressurised Aerosol
Active ingredient (micronised)
Acid B.P.
Trichlorofluoromethane B.P
Dichlorodifluoromethane B.P The active ingredient is micronised in a fluid energy mill to a fine particle size range. The oleic acid is mixed with the trichlorofluoromethane at a temperature of 10°–15° C. and the micronised drug is mixed into this solution with a high shear mixer. The suspension is metered into aluminium aerosol cans and suitable metering valves, delivering a metered dose of 85 mg of suspension, are crimped onto the cans and the dichlorodifluoromethane is pressure filled into the cans through the valves.

| Syrup | mg/5 ml dose |
|---|---|
| Active ingredient | |
| Sucrose B.P. | 100.00 |
| Glycerine B.P. | 2750.00 |
| | 500.00 |
| Buffer | |
| Flavour | |
| Colour | as required |
| Preservative | |
| Distilled Water to | 5.00 ml |

The active ingredient, buffer, flavour, colour and preservative are dissolved in some of the water, and the glycerine is added. The remainder of the water is heated to 80° C. and the sucrose is dissolved in this and cooled. The two solutions are combined, adjusted to volume and mixed. The syrup produced is clarified by filtration.

| Injection for Intravenous Administration | |
|---|---|
| Active ingredient | 50 mg |
| Water for injections B.P. to | 5 ml |

Sodium chloride or any other suitable material may be added to adjust the tonicity of the solution and the pH may be adjusted to that of maximum stability of the active ingredient using dilute acid or alkali or by the addition of suitable buffer salts. The solution is prepared, clarified and filled into appropriate sized ampoules sealed by fusion of the glass. The injection is sterilised by heating in a autoclave using one of the acceptable cycles. Alternatively the solution may be sterilised by filtration and filled into sterile ampoules under aseptic conditions. The solution may be packed under an inert atmosphere of nitrogen.

We claim:

1. Compounds of the general formulae (1a) and (1b)

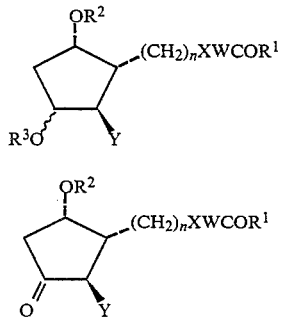

wherein $R^1$ is
(a) $-OCH(CO_2R^4)_2$;
(b) $-A(CH_2)_mB(CH_2)_nR^6$ where A and B are $-O-$ or $-S-$; m is 1–3, n is 0–3 and $R^6$ is phenyl;
(c) $-OR^9$ where $R^9$ is $C_{3-6}$ alkynyl or thienylmethyl;
(d) $-OCH(CH_2OH)_2$;

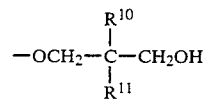

where
$R^{10}$ is $-OH$ or $-CH_2OH$ and $R^{11}$ is a hydrogen atom, $C_{1-4}$ alkyl or $-CH_2OH$; or

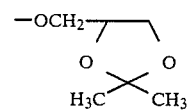

n is 1 or 2;
W is straight or branched $C_{1-7}$ alkylene;
X is cis or trans $-CH=CH-$ or $-CH_2CH_2$;
Y is a saturated heterocyclic amino group (attached to the cyclopentane ring via the nitrogen atom) which has 5–8 ring members and (a) optionally contains in the ring $-O-$, $-S-$, $-SO_2$, or $-NR^{12}$ (where $R^{12}$ is a hydrogen atom, $C_{1-7}$ alkyl or aralkyl having a $C_{1-4}$ alkyl portion); and/or (b) is optionally substituted by one or more $C_{1-4}$ alkyl groups;
$R^2$ is (i) $C_{1-5}$ alkyl substituted by (a) phenyl, (b) thienyl or (c) naphthyl (optionally substituted by $C_{1-4}$ alkyl or $C_{1-4}$alkoxy) or (ii) cinnamyl;
$R^3$ is a hydrogen atom or $C_{1-5}$ alkanoyl;
and the physiologically acceptable salts and solvates thereof.

2. Compounds as claimed in claim 1 in which Y is morpholino or piperidino and $R^2$ is a $C_{1-5}$ alkyl group substituted by phenyl, which phenyl is substituted by phenyl, ($C_{1-4}$ alkyl)phenyl or ($C_{1-4}$ alkoxy)phenyl 3. Compounds as claimed in claim 1 in which n is 2, X is cis $-CH=CH$ and W is $-CH_2CH_2-$.

4. Compounds as claimed in claim 1 in which $R^1$ is 2-propynyloxy, thienylmethoxy, $-OCH_2CH(OH)CH_2OH$ or the group (f).

5. Compounds as claimed in claim 1 having the formfula (1a) in which $-OR^3$ is in the $\beta$-position and $R^3$ is a hydrogen atom or acetyl.

6. Compounds as claimed in claim 1 having the formula (1a) in which $-OR^3$ is in the $\beta$-position and:
n is 2, X is cis $-CH=CH-$ and W is $-CH_2CH_2-$,
Y is piperidino or morpholino,
$R^2$ is benzyl in which the phenyl group is substituted by phenyl (which phenyl is optionally substituted by $C_{1-4}$ alkyl or $C_{1-4}$ alkoxy),
$R^3$ is a hydrogen atom,
$R^1$ is 2-propynyloxy or thienylmethoxy, and the physiologically acceptable salts and solvates thereof.

7. Compounds as claimed in claim 1 in which:
n is 2, X is cis $-CH=CH-$ and W is $-CH_2CH_2-$, and $R^2$ is benzyl in which the phenyl group is substituted by phenyl (which phenyl is optionally substituted by $C_{1-4}$ alkyl or $C_{1-4}$ alkoxy), and
(a)
  the compounds are of formula (1a) in which $-OR^3$ is in the $\beta$-position, Y is piperidino or morpholino and
  $R^3$ is a hydrogen atom or acetyl and $R^1$ is $-OCH_2CH(OH)-CH_2OH$ or the group (f)
or
(b)

the compounds are of formula (1a) in which —OR$^3$ is in the α-position, Y is piperidino and R$^3$ is a hydrogen atom and R$^1$ is —OCH$_2$CH(OH)CH$_2$OH, or (c) the compounds are of formula (1b), Y is morpholino or piperidino, and R$^1$ is —OCH$_2$CH(OH)CH$_2$OH or the group (f), and the physiologically acceptable salts and solvates thereof.

8. Compounds as claimed in claim 1 in which the carbon atom carrying the —(CH$_2$)$_n$XWCOR$^1$ group is in the R-configuration.

9. Compounds as claimed in claim 1 having the formula (1a) (in which the —OR$^3$ group is in the β-position and R$^3$ is a hydrogen atom) or the formula (1b), in which R$^1$ is a group of the types (a)-(c).

10. A pharmaceutical composition containing a compound as claimed in claim 1 and one or more pharmaceutical carriers.

* * * * *

UNITED STATES PATENT AND TRADEMARK OFFICE
CERTIFICATE OF CORRECTION

PATENT NO. : 4,530,925
DATED : July 23, 1985
INVENTOR(S) : ERIC W. COLLINGTON, ET AL.

It is certified that error appears in the above-identified patent and that said Letters Patent is hereby corrected as shown below:

Column 6, line 46, after "e.g. at" delete "31 70°" and substitute therefor -- -70° --;

Column 7, line 31, delete "formulaf" and substitute therefor -- formula --;

, line 33, delete "mayb" and substitute therefor -- may --;

Column 8, line 6, correct the first line of the preparation of Intermediate 1 by deleting "(+)" between "]-" and "-7" and substituting therefor -- (±) --;

, line 12, correct the second line of the preparation of Intermediate 2 by deleting "(+)" between "]-" and "-7" and substituting therefor -- (±) --;

, line 28, correct the first line of the preparation of Intermediate 5 by deleting "hydroxy" and substituting therefor -- Hydroxy --;

UNITED STATES PATENT AND TRADEMARK OFFICE
CERTIFICATE OF CORRECTION

PATENT NO. : 4,530,925

DATED : July 23, 1985

INVENTOR(S) : ERIC W. COLLINGTON, ET AL.

It is certified that error appears in the above-identified patent and that said Letters Patent is hereby corrected as shown below:

```
    Column 9, first line, after "=" insert -- + --
        before "42.8";

, line 27, delete "(b 92 mg)" and
                substitute therefor -- (92 mg) --;

Column 14, line 67, delete "1670 cm¹" and
        substitute therefor -- 1670 cm⁻¹ --;

Column 17, line 37, delete "1730 cm³¹ ¹" and
        substitute therefor -- 1730 cm⁻¹ --;

, last line, delete "]D" and substitite
                therefor -- ]D¹⁹ --;

Column 18, line 54, delete "1730 cm³¹ ¹" and
        substitute therefor -- 1730 cm⁻¹ --;
```

UNITED STATES PATENT AND TRADEMARK OFFICE
CERTIFICATE OF CORRECTION

PATENT NO. : 4,530,925

DATED : July 23, 1985

INVENTOR(S) : ERIC W. COLLINGTON ET AL.

It is certified that error appears in the above-identified patent and that said Letters Patent is hereby corrected as shown below:

Column 22, claim 1, delete lines 28-30 and substitute therefor

-- $R^2$ is (i) $C_{1-5}$ alkyl substituted by (a) phenyl [optionally substituted by $C_{1-6}$ alkyl, $C_{5-7}$ cycloaklyl, phenylalkyl having a $C_{1-3}$ alkyl portion, thienyl or phenyl (optionally substituted by $C_{1-4}$ alkyl, $C_{1-4}$ alkoxy or phenyl)], (b) thienyl [optionally substituted by $C_{5-7}$ cycloalkyl or phenyl (optionally substituted by $C_{1-3}$ alkyl, $C_{1-3}$ alkoxy or halogen)] or (c) naphthyl (optionally substituted by $C_{1-4}$ alkyl or $C_{1-4}$ alkoxy) or (ii) cinnamyl; --

Signed and Sealed this

Nineteenth Day of April, 1988

Attest:

DONALD J. QUIGG

*Attesting Officer*      *Commissioner of Patents and Trademarks*